United States Patent [19]

Parthasarathy et al.

[11] 4,121,039

[45] Oct. 17, 1978

[54] PROCESS FOR PRODUCING AN UNSATURATED GLYCOL DIESTER USING A CATALYST COMPRISING PALLADIUM CONTAINING THORIUM AS A PROMOTOR

[75] Inventors: R. Parthasarathy; Eugene Victor Hort, both of Wayne, N.J.

[73] Assignee: GAF Corporation, New York, N.Y.

[21] Appl. No.: 836,479

[22] Filed: Sep. 26, 1977

[51] Int. Cl.$^2$ .............................................. C07C 67/05
[52] U.S. Cl. ................................ 560/244; 260/410.6; 560/1; 560/112
[58] Field of Search .......................... 560/244, 1, 112; 260/410.6

[56] References Cited

U.S. PATENT DOCUMENTS

| 3,742,039 | 6/1973 | Ono | 560/244 |
| 3,922,300 | 11/1975 | Onoda | 560/244 |
| 4,038,307 | 7/1977 | Weitz | 560/244 |

FOREIGN PATENT DOCUMENTS 2,021,903 10/1970 Fed. Rep. of Germany ........... 560/244

*Primary Examiner*—James O. Thomas, Jr.
*Assistant Examiner*—Michael Shippen
*Attorney, Agent, or Firm*—Walter C. Kehm; W. Katz

[57] ABSTRACT

Unsaturated glycol diesters are prepared at high reaction rates, high degrees of conversion and high selectivity, by reacting a conjugated diene, a carboxylic acid and oxygen, in the presence of an improved active solid catalyst, in the liquid phase. The improved catalyst of the invention comprises palladium containing thorium as a promotor. In the preferred embodiment, butadiene and acetic acid are reacted with oxygen to produce the desired 1,4-diacetoxy-2-butene at high conversions and selectivity.

16 Claims, No Drawings

PROCESS FOR PRODUCING AN UNSATURATED GLYCOL DIESTER USING A CATALYST COMPRISING PALLADIUM CONTAINING THORIUM AS A PROMOTOR

BACKGROUND OF THE INVENTION

1. Field of the Invention

This invention relates to a process for preparing an unsaturated glycol diester from a conjugated diene compound. More particularly, it is concerned with an improved process for preparing the desired 1,4 diester in high conversion and selectivity by reacting a conjugated diene, a carboxylic acid and oxygen in the presence of a solid catalyst in the liquid phase.

2. Description of the Prior Art

It is known in the prior art to prepare an unsaturated glycol diester, such as 1,4-diacetoxy-2-butene by reaction of butadiene, acetic acid and oxygen in the presence of a solid catalyst, such as palladium containing one or more metals as promotors. Such a process is described in U.S. Pat. No. 3,755,423; U.S. Pat. No. 3,742,039; U.S. Pat. No. 3,723,510; U.S. Pat. No. 3,671,577; German Pat. No. 2,354,218; German Pat. No. 2,419,921; German Pat. No. 2,417,658 and German Pat. No. 2,415,248. The diester product then can be readily hydrogenated and hydrolyzed to 1,4-butanediol, an important industrial solvent and chemical intermediate.

A major disadvantage of the prior processes is that the activity or selectivity, or both, of the catalyst in the reaction is poor, and accordingly, high conversion of the diene into the desired product gives considerable amounts of undesirable by-products.

Accordingly, a need exists for a catalyst system which is capable of producing the desired product at high conversion rates without an increase in unwanted by-products. Of particular importance is the need to provide a catalyst which can promote the desired conversion of butadiene to 1,4-diacetoxy-2-butene or the corresponding 3,4 product which can be readily isomerized to 1,4, but without forming in any significant amount the 1,3 isomer simultaneously, the latter being incapable of isomerization into the desired 1,4 product.

SUMMARY OF THE INVENTION

What is described herein is an improved process for the production of unsaturated glycol diesters, more particularly, 1,4 diester, which comprises reacting in the liquid phase a conjugated diene, a carboxylic acid and oxygen in the presence of a solid catalyst consisting essentially of palladium containing thorium as a promotor supported on a suitable carrier. In the preferred form of the invention, butadiene, acetic acid and oxygen are reacted using, as the catalyst, palladium containing thorium, and optionally, also including bismuth, antimony, tellurium or selenium alone, or in combination with the other metals. The presence of thorium, with palladium, not only substantially improves the conversion of butadiene to the desired 1,4 or 3,4-diacetoxy-2-butenes, but it achieves this result selectively, that is, without producing appreciable amounts of the undesired 1,3-diacetoxy butene by-product.

DETAILED DESCRIPTION OF THE PREFERRED EMBODIMENTS

The conjugated diene which can be used in the process of the present invention may be butadiene or a hydrocarbon substituted butadiene derivative such as isoprene, 2,3-dimethylbutadiene, piperylene, etc., represented by the formula:

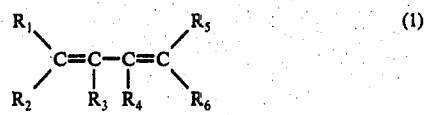

wherein $R_1$ to $R_6$ are individually a hydrogen atom or a hydrocarbon group, more preferably an alkyl group. Exemplary of suitable substituted butadienes include isoprene, 2,3-dimethylbutadiene, piperylene etc. In the case of hydrocarbon group substitution, the number of carbon atoms is preferably below 6, although it is not particularly limited. Butadiene and isoprene are preferred and butadiene is most preferred.

It is not necessary that the conjugated diene be in a purified form and it may contain inert gases such as nitrogen, etc., or a saturated hydrocarbon such as methane, ethane, butane, etc.

The carboxylic acid used may be any aliphatic, alicylic, or aromatic. Suitable carboxylic acids include, benzoic acid, cylohexane carboxylic acid, or the like. It is industrially advantageous to use a lower aliphatic carboxylic acid, such as acetic acid, propionic acid or butyric acid, etc. Acetic acid is particularly preferable, and when used the reaction proceeds as:

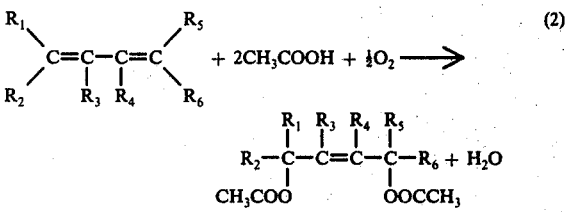

wherein $R_1$ to $R_6$ are as defined above.

The preparation of an unsaturated glycol diester according to the process of the present invention is carried out in the presence of a solid catalyst containing palladium and in addition, thorium and, optionally, antimony, bismuth, tellurium, selenium or a combination thereof. Although the reaction will proceed very slowly when reacting a conjugated diene, a carboxylic acid and molecular oxygen in the presence of a solid catalyst containing palladium only, when thorium is also present, the reaction velocity is remarkably increased. Furthermore, when using the solid two-component catalyst containing palladium and thorium, a remarkably increased conversion and a high selectivity to the desired unsaturated glycol diester is attained.

The catalyst may be used in the form of an alloy composed of palladium and thorium, and optionally antimony, also bismuth, tellurium and selenium, or, alternatively, the components of the catalyst may be supported on a suitable carrier.

In order to prepare a supported catalyst, ordinary preparation techniques for supporting a metallic catalyst on a carrier may be used. That is, the catalyst may be prepared by supporting an appropriate palladium compound and a thorium compound, and, optionally, an antimony, bismuth, tellurium and selenium compound on a carrier, and then subjecting the compounds to reducing conditions. These catalyst components may be easily reduced to metals by conventional techniques.

For example, the catalyst may be prepared by placing a carrier into a solution obtained by dissolving a palladium compound and a thorium compound, and optionally another metallic compound in an appropriate solvent, removing the solvents by distillation to deposit the above components on the carrier and, thereafter, reducing the compounds in a gaseous stream of hydrogen or other reducing agent such as hydrazine or formalin to their free metal states. The supported catalyst may also be prepared by placing a carrier into a solution of a palladium salt and a thorium salt, and, optionally, another metallic salt, and subsequently adding a precipitant such as, for example, an alkali, to precipitate the components onto the carrier, and thereafter subjecting the components to reducing conditions as described above.

The palladium and thorium may be simultaneously or successively supported onto the carrier.

The palladium compound used for preparing the catalyst is not especially limited, although a halogenated palladium, such as palladium chloride, an organic acid salt such as palladium acetate, palladium nitrate, palladium oxide, etc. are preferable in view of cost. However, other palladium compounds, for example, sodium palladium chloride, sodium palladium sulfate, etc. can be used, of course.

In general, the concentration of palladium on the carrier is preferably within the range of 0.1 to 10% and most preferably, 0.5 to 5%. The thorium, expressed as $ThO_2$, suitably is in the range of 0.01 to 15% and preferably, 0.05 to 5%.

Also the thorium compound and the optional metal, used for preparing the catalyst may suitably be any of the compounding halides, nitrates, sulfides, oxides or other various compounds as is well known. If desired, thorium metal may be used.

Suitable carriers for use in the preparation of a supported catalyst include activated carbon, silica gel, silica-alumina, alumina clay, bauxite, magnesia, diatomaceous earth, pumice, etc. Activated carbon is a preferred carrier.

When activated carbon is used as the carrier, if it is prior treated with an appropriate oxidizing agent, the catalytic activity will be enhanced and a 1,4 glycol diester can be produced in high yields and high degrees of selectivity. Oxygen, air, carbon dioxide, steam, nitric acid, chromic acid solution, various kinds of perhydroxy acid, peracid, etc. are appropriate oxidizing agents. The oxidation treatment of activated carbon may be carried out simultaneously with the deposition of the active components. For example, a catalyst having a similarly high activity as prior activated carbon is obtained by dissolving a palladium compound and the thorium compound in an oxidizing agent such as nitric acid, impregnating the activated carbon with the resulting solution and then reducing the component to prepare the catalyst.

The reaction of conjugated diene with carboxylic acid according to the process of the present invention can be carried out by using any conventional method, such as a fixed bed type, a fluid bed type, a suspension catalyst type, trickle-bed, etc. For example, the reaction can be easily carried out by suspending a catalyst in a reaction medium comprising a carboxylic acid, and then passing a conjugated diene and a molecular oxygen-containing gas therein. The molecular oxygen-containing gas is not necessarily pure oxygen, but may be oxygen diluted with an inert gas, e.g. air. The amount of oxygen to be used is not critical, but preferably is within the range of 1 to 60 mole percent based on the total components of feed gases.

The reaction may be carried out in the anhydrous state, but the presence of water up to about 10%, but not exceeding 30%, is preferable.

In addition to the above described carboxylic acids, acid anhydrides, carboxylates of alkali metals or alkaline earth metals, such as lithium, sodium, potassium, magnesium, calcium, etc., or inert organic solvents, e.g. saturated hydrocarbons, esters, etc., may be present in the reaction medium. The amount of carboxylic acid reactant is preferably above 50% based on the weight of reaction medium.

The reaction can be carried out at temperatures as low as about 20° C. Considering the reaction velocity and the yield of desired product, the preferred reaction temperature range is 60° to 180° C. The reaction pressure is not critical, but the reaction is usually carried out under atmospheric or superatmospheric pressures of up to 100 kg./cm$^2$. Of course, it can be carried out under even higher pressures if desired.

One particularly advantageous form of the process of the invention is the trickling phase mode in which acetic acid together with butadiene which is present in dissolved and/or gaseous form or in a mixed phase, trickles in an oxygen atmosphere over a fixed bed catalyst in a tubular reactor. In this arrangement, glacial acetic as well as the other reactants (hydrocarbon and oxygen) move downwardly over the catalyst. Alternatively, the catalyst can be distributed as a powder in the acetic acid and the mixture of hydrocarbon and oxygen bubbled into the suspension in a batch type operation.

According to the process of the present invention, both a remarkably increased conversion and a high degree of selectivity to the desired product is attained in the preparation of an unsaturated glycol diester from a conjugated diene as compared with the prior art methods. The process of the present invention is extremely advantageous as an industrial method for manufacturing an unsaturated glycol diester, since there is very little, if any, loss of expensive catalyst component so that recovery and purification after-treatment is quite easy.

The present invention will be further illustrated in detail with respect to the following examples which are presented for purposes of illustration only and are not intended to be limiting of the scope of the invention unless otherwise so specified.

In the following examples, "Conversion" refers to the percentage of starting material, butadiene, consumed in the reaction and "Selectivity" is the percentage of cis- and trans-1,4-diacetoxy-2-butene produced as compared to the total butadiene consumed.

Other terms used in the examples are defined as follows:

DAB: diacetoxybutene
3,4-DAB: 3,4-diacetoxy-1-butene
1,4-DAB: 1,4-diacetoxy-2-butene
trans-1,4-DAB: trans-1,4-diacetoxy-2-butene
cis-1,4-DAB: cis-1,4-diacetoxy-2-butene
1,3-DAB: 1,3-diacetoxybutene Each isomer of diacetoxybutene shown in the examples, after being separated by gas chromatography, is identified by its NMR and mass spectra.

EXAMPLES OF INVENTION

EXAMPLE 1

Preparation of Catalyst

A mixture of 2.92 mmols of palladium nitrate and 1.974 mmols of thorium nitrate was dissolved in 50 ml of aqueous nitric acid solution (1 part conc. $HNO_3$ to 1 part $H_2O$). Then 20 g of acid-washed 12 to 30 mesh activated carbon was slurried into the above solution and dried slowly over a water bath. The dried material was further dried in a flowing nitrogen stream for 1.5 hrs. and reduced in a stream of nitrogen saturated with methanol at room temperature, at 200° C. for 2 hrs., and further at 400° C. for 1 hr.

EXAMPLE 2

Preparation of DAB using Pd and Th Catalyst

A stainless steel reactor tube with internal diameter of 1 inch and 12 inches in length was packed with 18.4 g of the catalyst of Example 1 and glacial acetic acid was trickled through at the rate of 30 ml/hr. Then butadiene at 55 mmols/hr and oxygen at 110 mmols/hr were introduced into the reactor at a gauge pressure of 15 psi to produce a continuous reaction at an average reaction temperature of 107° C. Under these conditions, a 66.8% conversion of butadiene and 81.7% selectivity to cis- and trans-1,4-DAB were obtained. Selectivity to 3,4-DAB was 12.5%; thus the total useful diacetate selectivity was 94.5%. Only 0.7% 1,3-DAB was produced as a by-product. The amount of eluted palladium was negligible.

EXAMPLE 3

Preparation of DAB Using Pd and Th and Bi Catalyst

A catalyst was prepared in the same manner as described in Example 1 except that bismuth was included. Accordingly, bismuth nitrate was added to the impregnating solution to give a final composition containing 2.92 mmols Pd, 0.78 mmols Th and 0.42 mmols Bi. 18.1 g of this catalyst was charged into the reactor and the reaction was carried out in the same manner as described in Example 2. The reaction temperature was 103°. This catalyst converted 82.8% of butadiene to give a cis + trans-1,4 DAB selectivity of 86.3% and a 3,4-DAB selectivity of 9.7%. The combined useful selectivity was 96%. The 1,3-DAB by-product amounted to less than 0.05%. The amount of eluted palladium was negligible.

EXAMPLE 4

Preparation of DAB Using Pd and Th and Bi(High) Catalyst

A catalyst was prepared as described in Example 1 except, that a greater portion of bismuth was used. Accordingly, bismuth nitrate was included in the impregnating solution to give a final composition containing 2.92 mmols Pd, 0.78 mmols Th and 0.84 mmols Bi. This catalyst was used in the same manner as in Example 3. At a reaction temperature of 104°, butadiene conversion was 80.1%. The cis + trans-1,4 DAB selectivity was 87.6%, and the 3,4-DAB selectivity was 8.4%, giving a combined useful diacetate selectivity of 96%. The 1,3-DAB selectivity was only 0.9%. The amount of palladium eluted was negligible.

EXAMPLE 5

Preparation of DAB Using Pd and Te (Comparative Example)

A Pd-Te catalyst containing 5 mmols Pd and 1.5 mmols Te was prepared according to Example 26 of U.S. Pat. No. 3,755,423. Accordingly, 19.8 g of this catalyst was charged into the reactor and glacial acetic acid was poured through at the rate of 30 ml/hr. Butadiene and oxygen at 110 mmols/hr were introduced into the reactor, which was maintained at 15 psig and a reaction temperature of 109°. Under these conditions the conversion of butadiene was only 23% and cis + trans-1,4-DAB selectivity was 85.7%. The 3,4-DAB selectivity was 11.2%, giving a combined diacetate selectivity of 96.9%. The 1,3-DAB selectivity was a very high 3.1%.

EXAMPLE 6

Preparation of DAB Using Pd and Te (Without Cl−) (Comparative Example)

Another Pd-Te catalyst was prepared in the same manner as Example 5 except the activated carbon carrier was first impregnated with a solution of palladium diacetate in glacial acetic acid to eliminate the deleterious effect of chloride ion on the catalyst. A nitric acid solution of tellurium dioxide was used to introduce the tellurium in the catalyst. The finished catalyst contained 2 mmols of Pd and 3.26 mmols of Te. This catalyst was evaluated in the same manner as Example 2 except that an oxygen flow of 220 mmols/hr was used. At a reaction temperature of 102°, the Pd-Te catalyst gave a butadiene conversion of only 49.4% with a cis + trans-1,4-DAB selectivity of 91.1%, and a 3,4-DAB selectivity of 8.9%.

EXAMPLE 7

Preparation of DAB Using Pd and Bi Catalyst (Comparative Example)

The Pd-Bi catalyst of Example 49 of U.S. Pat. No. 3,755,423 is described as giving only a 21% conversion of butadiene and a large amount of eluted palladium.

Having now fully described the invention, it will be apparent to one of ordinary skill in the art that many changes and modifications can be made thereto without departing from the spirit or scope of the invention as set forth herein.

Accordingly, what is claimed as new and desired to be secured by Letters Patent is:

1. A process for the production of unsaturated diesters, which comprises reacting in a liquid phase a conjugated diene of the formula:

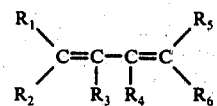

wherein $R_1$, $R_2$, $R_3$, $R_4$, $R_5$ and $R_6$ may be same or different and each represents hydrogen or an alkyl group having 1 to 6 carbon atoms, a carboxylic acid selected from the group consisting of aliphatic, aromatic and alicyclic carboxylic acid having 2 to 20 carbon atoms, and oxygen in the presence of a supported solid catalyst consisting essentially of elemental palladium containing thorium as a promotor.

2. A process for the production of unsaturated diesters, which comprises reacting in a liquid phase a conjugated diene of the formula:

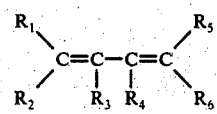

wherein $R_1$, $R_2$, $R_3$, $R_4$, $R_5$ and $R_6$ may be same or different and each represents hydrogen or an alkyl group having 1 to 6 carbon atoms, a carboxylic acid selected from the group consisting of aliphatic, aromatic and alicyclic carboxylic acid having 2 to 20 carbon atoms, and oxygen in the presence of a supported solid catalyst consisting essentially of elemental palladium containing thorium as a promotor, in which the catalyst also includes at least one additional metal selected from the group consisting of bismuth, antimony, tellurium and selenium.

3. A process according to claim 1 wherein the concentration of palladium on the carrier is within the range of 0.1 to 10%.

4. A process according to claim 3 wherein said range is 0.5 to 5%.

5. A process according to claim 1 wherein said thorium is present in the range of 0.01 to 15%, expressed as $ThO_2$.

6. A process according to claim 5 wherein said range is 0.05 to 5%.

7. The process according to claim 1 in which the conjugated diene is butadiene, isoprene, 2,3-dimethylbutadiene or piperylene.

8. The process according to claim 1 in which the catalyst is prepared by supporting a palladium compound and thorium on a carrier and then reducing said supported compounds with a reducing agent.

9. The process according to claim 3 in which the carrier is activated carbon.

10. A process for the production of diacetoxybutene, which comprises reacting butadiene, acetic acid and oxygen in the liquid phase in the presence of a supported solid catalyst consisting essentially of elemental palladium and thorium as a promotor.

11. A process for the production of diacetoxybutene, which comprises reacting in a liquid phase butadiene, acetic acid and oxygen in the presence of a supported solid catalyst consisting essentially of elemental palladium containing thorium as a promotor, in which the catalyst also includes at least one additional metal selected from the group consisting of bismuth, antimony, tellurium and selenium.

12. A process according to claim 10 in which the concentration of palladium on the carrier is within the range of 0.1 to 10%.

13. A process according to claim 12 wherein said range is 0.5 to 5%.

14. A process according to claim 10 wherein said thorium is present in the range of 0.01 to 15%, expressed as $ThO_2$.

15. A process according to claim 14 wherein said range is 0.05 to 5%.

16. A process according to claim 10 wherein said support is activated carbon.

* * * * *